United States Patent
McCoy

Patent Number: 5,405,411
Date of Patent: Apr. 11, 1995

[54] ARTICULATED ANKLE JOINT WITH INNER AND OUTER RACES FOR UNIVERSAL MOVEMENT

[76] Inventor: Allen J. McCoy, 18790 McCoy Rd., Livingston, La. 70754

[21] Appl. No.: 861,593

[22] Filed: Apr. 1, 1992

[51] Int. Cl.⁶ .................................... A61F 2/66
[52] U.S. Cl. .......................... 623/49; 623/52; 403/111; 403/144
[58] Field of Search .............. 623/47, 48, 49, 50, 623/52, 55, 53; 403/144, 132, 120, 111

[56] References Cited

U.S. PATENT DOCUMENTS

| | | | |
|---|---|---|---|
| 288,239 | 11/1883 | Ingram | 623/49 X |
| 1,368,348 | 2/1921 | Moore | 623/49 |
| 1,643,720 | 9/1927 | McKone | 403/144 X |
| 2,289,154 | 7/1942 | Van Cise | . |
| 2,309,281 | 1/1943 | Steele | 623/53 X |
| 2,470,480 | 5/1949 | Fogg | . |
| 2,594,752 | 4/1952 | Fahlström | 403/120 X |
| 2,699,554 | 1/1955 | Comelli | 623/49 |
| 3,188,035 | 6/1965 | Owen | 403/111 X |
| 3,196,463 | 7/1965 | Farneth | . |
| 3,754,286 | 8/1973 | Ryan | 623/49 |
| 4,442,554 | 4/1984 | Copes | . |
| 4,718,913 | 1/1988 | Voisin | 623/49 |
| 4,764,172 | 8/1988 | McCoy | 623/49 |
| 5,030,239 | 7/1991 | Copes | 623/52 |

FOREIGN PATENT DOCUMENTS

0295807 12/1916 Germany .................. 623/55

*Primary Examiner*—David H. Willse

[57] ABSTRACT

An artifical ankle joint for use as an ankle between a foot prosthesis and leg prosthesis in an artificial limb. The artificial ankle joint includes a foot plate attached to a foot prosthesis, a leg plate attached to a leg prosthesis, a stem assembly and bearing assembly connected between the plates in which the bearing is a spherical bearing oriented vertically and including an inner race connected to the leg plate about an axis generally horizontal when the ankle joint is in use and an outer race connected with the stem assembly. Resilient structure extends between the plates for providing a degree of resistance to relative movement of the plates and includes a heel spring enclosing the stem assembly and a toe spring spaced from the heel spring with both the toe and heel springs extending between the plates. The stem includes a unitary or two piece unit anchored to the foot plate at one end and including a vertically disposed spherical bearing assembly connected to the leg plate at its other end to enable relative pivotal movement of the foot prosthesis in any angular direction with respect to the leg prosthesis and enabling limited swivelling movement of the foot prosthesis in relation to the leg prosthesis. This enables the articulated ankle to closely simulate all movement capabilities of a natural ankle.

13 Claims, 2 Drawing Sheets

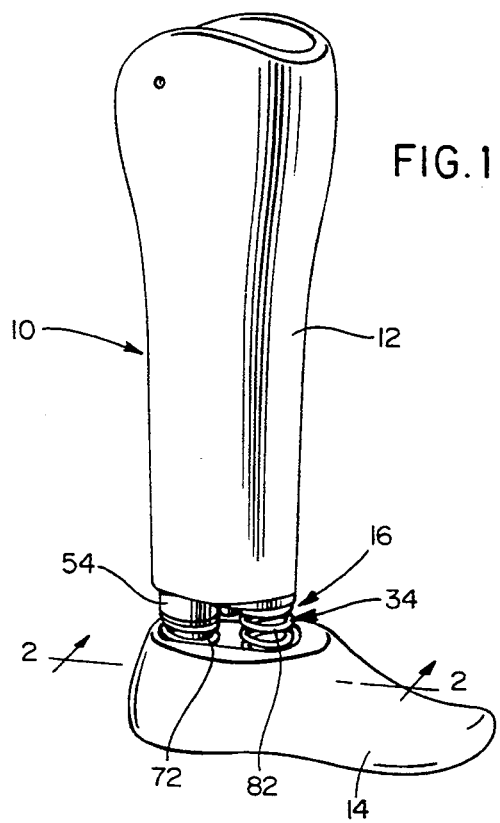
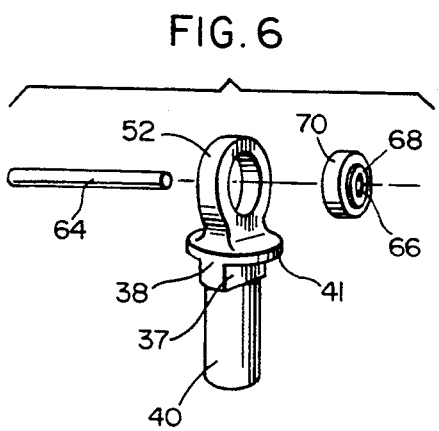
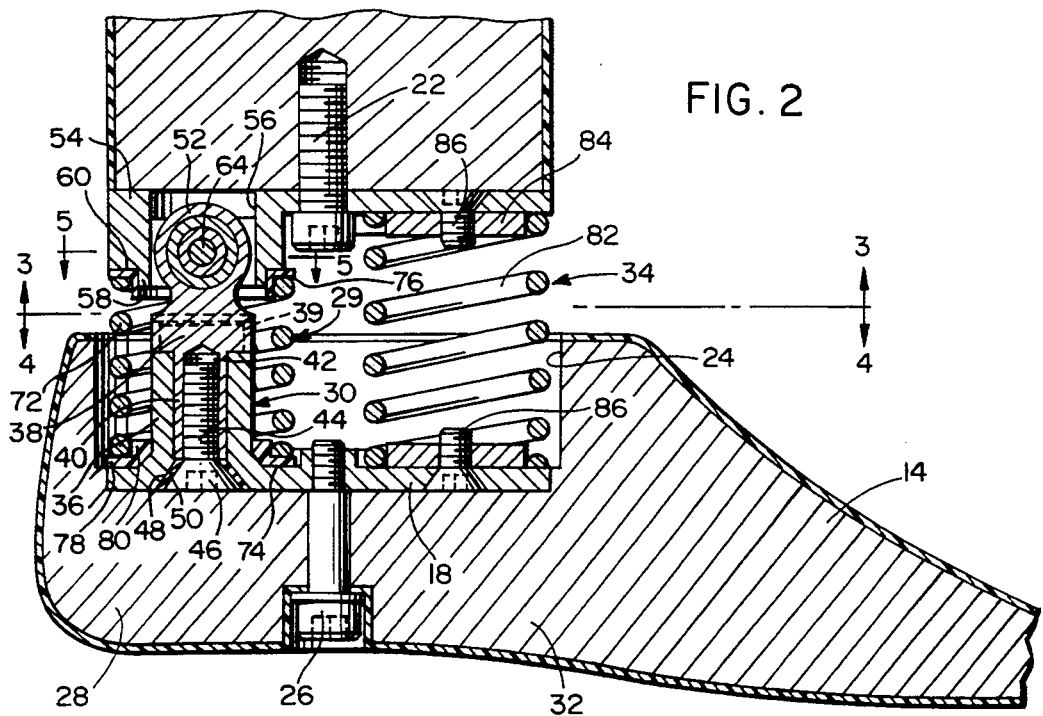

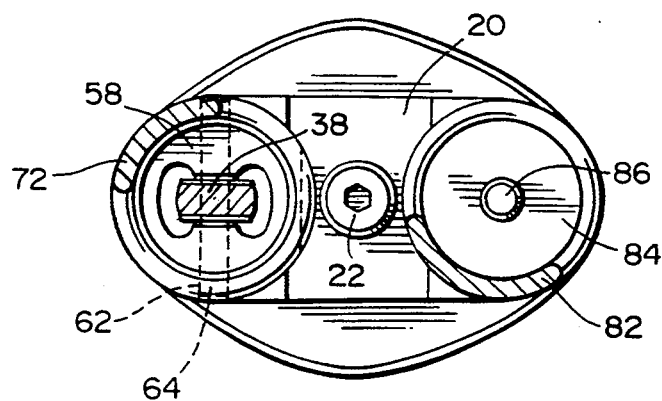
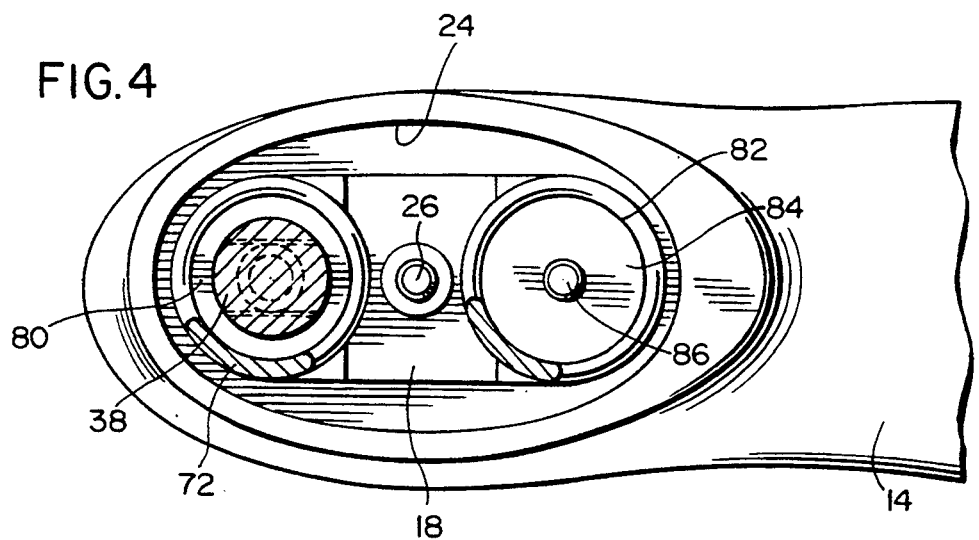
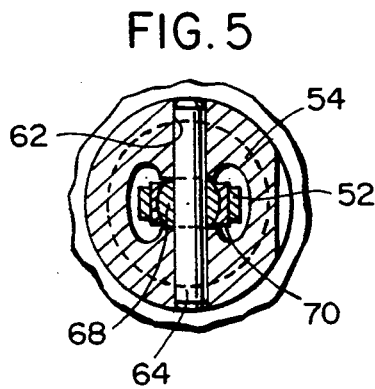
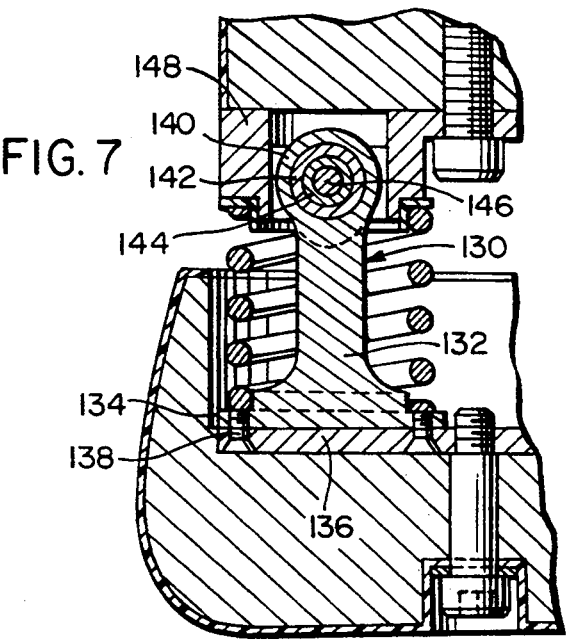

ARTICULATED ANKLE JOINT WITH INNER AND OUTER RACES FOR UNIVERSAL MOVEMENT

BACKGROUND OF THE INVENTION

1. Field of the Invention

The present invention generally relates to anatomical prostheses and more specifically an artificial ankle joint for use as an ankle between the foot prothesis and leg prosthesis in an artificial limb. The artificial ankle joint includes a foot plate attached to a foot prosthesis, a leg plate attached to a leg prosthesis, a stem assembly and bearing assembly connected between the plates in which the bearing is a spherical bearing oriented vertically and including an inner race connected to the leg plate about an axis generally horizontal when the ankle joint is in use and an outer race connected with the stem assembly and foot plate. Resilient structure extends between the plates for providing a degree of resistance to relative movement of the plates and includes a heel spring enclosing the stem assembly and a toe spring spaced from the heel spring with both the toe and heel springs extending between the plates. The stem includes a unitary or two piece unit anchored to the foot plate at one end and including a vertically disposed spherical bearing assembly connected to the leg plate at its other end to enable relative pivotal movement of the foot prosthesis in any angular direction with respect to the leg prosthesis and enabling limited swivelling movement of the foot prosthesis in relation to the leg prosthesis. This enables the articulated ankle to closely simulate all movement capabilities of a natural ankle.

2. Description of the Prior Art

My prior U.S. Pat. No. 4,764,172 for Articulated Ankle issued Aug. 16, 1988 discloses an ankle joint for use in an artificial limb which utilizes a foot plate, leg plate, stem and a heel spring and toe spring with the stem including a horizontally disposed bearing and a structure enabling adjustment of the stem and attachment of the stem to the foot and leg plates. This patent and the prior art cited of record in that patent are made of record herein. The prior art does not disclose the specific structure of the articulated ankle joint of this invention including the specific arrangement of the stem and vertically disposed bearing interconnecting the stem and leg plate and cushioning spacers between the heel spring and plates. Attached hereto from the publication "Orthotics and Prosthetics" dated Spring 1987 is an article entitled "Dual-Ankle Spring (D.A.S.) Foot-Ankle System" by Jerome P. Voisin, which discloses the use of anterior and posterior springs between plates with an Achilles band controlling relative movement to some degree. This article discusses various problems and developments in this field of endeavor and certain of the developments relating to this subject matter including certain prior patents. This article also fails to disclose the specific structure of this invention.

SUMMARY OF THE INVENTION

An object of the present invention is to provide an articulated ankle joint that can be used in various activities including standing, walking, running, dancing, climbing and the like by individuals regardless of body weight, size and agility thereby enabling an amputee to perform almost any activity or function as well as a non-amputee with the foot movements of the amputee being substantially the same as foot movements of a non-amputee.

Another object of the invention is to provide an artificial ankle joint which includes a foot plate and a leg plate for attachment to a foot and leg prosthesis respectively combined with a stem assembly and bearing assembly interconnecting the plates in which the bearing is a spherical bearing oriented vertically and including an inner race connected to the leg plate about an axis generally horizontal when the ankle joint is in use and an outer race connected with the stem assembly. Resilient structure extends between the plates for providing a degree of resistance to relative movement of the plates and includes a heel spring encircling the stem and engaged with the plates and a toe spring engaged with the plates in spaced relation to the heel spring with the stem including the spherical bearing assembly at its upper end oriented vertically and connected to the leg plate by a transverse pin enabling pivotal movement of the foot prosthesis in relation to the leg prosthesis in all angular relations and enabling the foot prosthesis to swivel to a limited degree in relation to the leg prosthesis thereby enabling the artificial articulated ankle joint of this invention to perform all of the functions of a natural ankle and to perform those functions in a natural manner.

Still another object of the invention is to provide an articulated ankle joint in accordance with the preceding objects in which the stem is a two piece assembly to facilitate assembly of the stem, heel spring and the leg and toe plates.

Still another object of the invention is to provide an articulated ankle joint which is relatively simple in construction, strong and durable in use, dependable and longlasting and effective to enable an amputee to perform all activities with respect to leg and foot movements in a manner closely simulating the movement capabilities of a natural ankle.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of an articulated ankle joint constructed in accordance with the present invention.

FIG. 2 is an enlarged sectional view taken substantially along section line 2—2 on FIG. 1.

FIG. 3 is a sectional view taken along section line 3—3 of FIG. 2.

FIG. 4 is a sectional view taken along section line 4—4 of FIG. 2.

FIG. 5 is a sectional view taken along section line 5—5 of FIG. 2.

FIG. 6 is an exploded perspective view of the post forming one component of the stem assembly and the association of the vertical spherical bearing assembly.

FIG. 7 is a fragmental sectional view similar to FIG. 2 and illustrating another form of a stem assembly.

DESCRIPTION OF THE PREFERRED EMBODIMENT

An artifical limb 10 is illustrated in FIG. 1 and includes a leg prosthesis 12, a foot prosthesis 14 and an articulated ankle joint 16 constructed in accordance with the present invention for connecting the foot prosthesis 14 to the leg prosthesis 12.

As illustrated in more detail in the drawings, the articulated ankle joint 16 includes a foot plate 18 and a leg plate 20, each of which is generally in the form of an oval-shaped plate with rounded ends. The leg plate 20 is secured to the base of the leg prosthesis 12 by a centrally located socket head cap screw 22. The foot plate 18 is secured in a well 24 in the foot prosthesis 14 by a socket head cap screw 26. Other methods may be used to secure the foot plate 18 and leg plate 20 to the foot and leg prostheses. The plates 18 and 20 are connected together at a heel portion 28 of foot prosthesis 14 by a heel spring 29 and stem assembly 30 and connected between the plates forwardly of the heel spring 29 and stem assembly 30 generally at the arch portion 32 of prosthesis 14 by a toe spring 34 with the springs forming a resistance to movement as described in detail hereinafter.

The stem assembly 30 includes an upwardly extending tubular projection 36 that is integral with the bottom plate 18. A post 38 is engaged with the upper end of the projection 36 and includes a depending axial sleeve 40 integral therewith which is telescopically received in the cylindrical projection 36. The interior of the sleeve 40 is internally threaded at 42 to receive an externally threaded cap screw 44 that has a tapered head 46 received in a countersunk opening 48 in the bottom plate 18 which communicates with the interior of the cylindrical projection 36. A frustro-conical lock washer 50 is positioned between the tapered outer surface of the head 46 and the inclined surface of the counter sunk opening 48. The head is provided with a polygonal socket to receive a suitable tool to enable the post 38 to be assembled with respect to the cylindrical projection 36. Relative rotation of the post 38 in relation to projection 36 is prevented by a pair of flats 37 on the post 38 which are telescoped into a transverse groove or recess 39 formed in the upper end of the projection 36. The post 38 includes a generally cylindrical cap 41 on its upper end which telescopes over the upper end of the projection 36 to assist in maintaining alignment and assembly and strengthening the connection between the projection 36 and post 38.

The upper end of the post 38 is provided with an annular ring 52 which is vertically disposed with the width of the ring being substantially less than the diameter of the post 38 with the ring having a generally horizontally disposed central axis perpendicular to the vertical axis of the post, sleeve and projection.

The top plate 20 includes a thickened heel portion 54 having a cavity 56 extending therethrough which forms a bearing housing and receives the ring 52 therein as illustrated in FIG. 2. The lower edge of the thickened portion is provided with a depending peripheral flange 58 which extends around the opening and defines a downwardly facing shoulder 60. The thickened portion 50 is provided with a transversely extending bore or passageway 62 which receives a spring pin 64 such as a roll pin which is secured in the bore 62 at the ends thereof with the central portion of the pin extending through the central opening 66 through the inner race 68 of a spherical bearing which includes an outer race 70 rigidly received in the ring 52 with the spherical bearing structure between the inner and outer races enabling the inner race and thus the pin and the outer race and thus the ring on the post 38 to move in any angular relation and also enabling limited swivelling movement of the foot prosthesis. With this construction, the foot plate 18 and leg plate 20 are securely and positively interconnected with the foot plate 18 being capable of universal movement in relation to the leg plate 20.

The heel spring 29 is in the form of a coil compression spring 72 which is positioned in encircling relation to the stem assembly outwardly of the flange 58 and slightly below the shoulder 60 at its upper end with the lower end being disposed adjacent the upper surface 74 of the foot plate 18. A cushioning spacer 76 of right angular cross sectional configuration is positioned between the upper end of the spring 72 and the shoulder 60 and flange 58 to cushion the upper end of the spring 72 in relation to the foot plate 20. A similar cushioning spacer 78 is provided between the lower end of the spring 72 and the surface 74 with the inner edge of the spacer 76 being upturned and thicker as indicated by reference numeral 80 with this portion of the spacer being positioned between the outer surface of the cylindrical projection 36 and the inner surface of the lower end of the spring 72 in the area adjacent the juncture between the projection 36 and the foot plate 18 as illustrated in FIG. 2. The spacers 76 and 78 are preferably constructed of plastic material such as nylon and serve to somewhat cushion the spring and prevent metallic sounds being produced by relative movements between the plates and spring.

The toe spring 34 includes a coil compression spring 82 which extends between and engages the inwardly facing opposed surfaces of the foot plate 18 and toe plate 20 with each end of the toe spring 82 receiving a toe spring insert 84 to which the end of the spring is secured with the inserts 84 being secured to the foot plate 18 and toe plate 20 respectively by countersunk flat head socket cap screws 86.

The bearing assembly and the annular ring at the upper end of the stem are oriented in a vertical plane and the cavity 56 forming the bearing housing provides sufficient clearance with respect to the annular ring 52 to enable universal movement of the stem assembly 30 in relation to the leg plate 20 with such movements being resisted by heel spring 72 and toe spring 82. Nylon spacer washers used at the upper and lower end of the rear or heel spring 72 eliminates noise due to relative movement between the spring and plates. The spacer washers are assembled at the top and bottom of the spring 72 when the ankle joint is assembled by loading the springs and inserting the transverse pin 64 through apertures in the bearing housing and the center of the inner race. The association of the spring 72 with the flanges and shoulders on the leg plate 20 and association of the lower end of the spring with the foot plate 18, the spacer 76 and the stem assembly 30 retain the heel spring in place whereas the inserts or clips 84 retain the toe spring 82 in place.

As illustrated in FIG. 7, a one-piece stem assembly 130 which includes a rigid one-piece post 132 provided with an enlarged base 134 at its lower end is rigidly mounted on foot plate 136 by fasteners 138 in the form of screw threaded members. The upper end of the post 132 includes a vertical annular ring 140 integral with the post and supporting a spherical bearing 142 therein with the inner race 144 of the bearing 142 receiving a pin 146 securing the inner race to the bearing housing or cavity 148. The function of this form of the invention is substantially the same as that shown in FIGS. 1–6.

The transverse axis of the spherical bearing is defined by the pin 64 or 146 extending through the inner race 68 or 144 of the spherical bearing and anchored to opposite sides of the bearing housing 56 or 148. The spherical bearing surfaces in the spherical bearing between the inner and outer race enables the bearing housing and leg plate to pivot, rotate, swivel in any direction within the limits defined by the spherical bearing and the clearance between the interior cavity and the bearing housing and the post and ring with all movements being resisted by the coil springs thereby providing an ankle joint which, when incorporated into an artificial leg and foot, will enable an amputee to perform all normal activities in a manner closely simulating the action and performance of a natural ankle. This is accomplished by the structural components enabling relative movement between the leg prosthesis and foot prosthesis in a universal direction to provide universal pivotal and swivel movement including inversion, eversion, fore and aft rocking, swivelling and tilting with all movements being cushioned and resisted and controlled by the coil springs which can be interchanged with other coil springs having different moduli of elasticity which enables the ankle joint to be used by individuals having different physical characteristics.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An articulated ankle joint comprising a foot plate for attachment to a foot prosthesis, a leg plate for attachment to a leg prosthesis, a stem assembly interconnecting said plates, said stem assembly being positioned at a heel portion of the foot prosthesis, said stem assembly including a spherical bearing for providing relative movement between the plates, a heel coil spring encircling the stem assembly and engaging said plates for reacting between the plates and providing a degree of resistance to said relative movement between the plates, and a toe coil spring connected between the plates forwardly of the stem assembly for providing resistance to said relative movement between the plates, said spherical bearing being vertically disposed and including an inner race connected with said leg plate and an outer race connected with said stem assembly, said stem assembly including a vertically disposed annular ring receiving said outer race, said inner and outer races of the spherical bearing including partial spherical surfaces to enable universal movement between the inner race and outer race, said leg plate including a bearing housing having a cavity therein receiving said ring and spherical bearing, a retaining pin extending transversely of said cavity and through said inner race and into said bearing housing thereby connecting said inner race to the leg plate for relative movement between the bearing housing and stem assembly.

2. The joint as defined in claim 1 wherein said stem assembly is connected with said foot plate with the annular ring being rigid with the upper end of the stem assembly, said heel spring engaging the foot plate in peripheral encircling relation to the stem assembly and engaging the leg plate in encircling relation to the bearing housing and ring to resiliently resist relative movement between the plates.

3. The joint as defined in claim 1 wherein said stem assembly includes a cylindrical projection integral with the foot plate and extending upwardly therefrom, a post engaging the upper end of the projection and including a depending sleeve telescopically engaging the projection, said annular ring being integral with the post and fastening means extending through the projection and securing the sleeve to the projection to enable assembly of the components and loading of the springs during assembly.

4. The ankle joint as defined in claim 3 wherein the upper end of said projection and said post include interengaging socket and projection means to preclude relative rotational movement between said projection and said post in spaced relation to said fastening means.

5. The ankle joint as defined in claim 1 wherein said stem assembly includes an upstanding tubular projection rigid with said foot plate, a post engaging the upper end of the projection, a sleeve depending from said post and telescoped into said projection, said sleeve being internally threaded, and a screw threaded fastener extending through the foot plate and threaded into said sleeve for rigidly mounting the post on said projection.

6. An articulated ankle joint comprising a foot plate for attachment to a foot prosthesis, a leg plate for attachment to a leg prosthesis, a stem assembly interconnecting said plates, said stem assembly including a generally vertically oriented spherical bearing for allowing relative movement of the plates, said spherical bearing including an inner race, horizontally disposed pin means connecting said leg plate to said inner race, an outer race rigid with said stem assembly, and resilient means between the plates for providing a degree of resistance to relative movement of the plates with respect to each other, said stem assembly including post means rigid with and upstanding from said foot plate, said spherical bearing being mounted at the upper end of said post means and oriented in a vertical plane, said horizontal pin means being disposed transversely of said foot prosthesis and said leg prosthesis and enabling relative pivotal and rotational movement of said plates, said leg plate including a vertically disposed cavity receiving said spherical bearing and an upper end of said post, said pin means extending transversely of said cavity and through said inner race, said resilient means including a pair of spaced coil springs connected to said plates, one of said springs being at the heel portion of the plates and the other spring being at the toe portion of the plates.

7. The ankle joint as defined in claim 6 wherein said post is of one-piece construction and includes a base, fastener means rigidly securing said base to said foot plate.

8. The ankle joint as defined in claim 6 wherein said post is of two-piece construction and including a lower part of unitary construction with the foot plate and fastener means securing an upper part of the post to the lower part.

9. The ankle joint as defined in claim 8 wherein said upper and lower parts of said post are telescopic and include means preventing relative rotation.

10. The ankle joint as defined in claim 6 wherein said coil spring at the heel portion of the plates being disposed in enclosing relation to said post means and having an upper end engaged with said leg plate in peripheral relation to said cavity to resist relative movement of said plates in all directions permitted by said spherical bearing and pin means.

11. The ankle joint as defined in claim 10 wherein said post means includes a tubular projection extending upwardly from said foot plate and including a hollow interior and a post member having a downwardly facing horizontal flange engaged with an upper end of said projection and a screw threaded fastener extending into threaded engagement with the post member through said projection to enable assembly of the ankle joint and loading of said springs.

12. The ankle joint as defined in claim 10 wherein said post means includes a one piece post having a base attached to said foot plate and the spherical bearing at an upper end thereof received in said cavity, said spring at the heel portion of the plates encircling the one piece post and having an upper end engaged with said leg plate at a lower end of said cavity to resist relative movement between said plates in all directions.

13. The ankle joint as defined in claim 12 wherein said post member includes a tubular sleeve telescoped into said projection with the sleeve being internally threaded for threaded engagement by said threaded fastener, an upper end of said projection and said flange on said post member including interengaging radial recess means and projection means to prevent rotation of the post member in relation to the projection when the post member and projection are assembled by threading the fastener into said sleeve.

* * * * *